(12) United States Patent
Ingman

(10) Patent No.: US 7,294,349 B2
(45) Date of Patent: Nov. 13, 2007

(54) WRINKLE CREAM

(75) Inventor: Dov Ingman, Haifa (IL)

(73) Assignee: Or Le Or Ltd., Haifa (IL)

( * ) Notice: Subject to any disclaimer, the term of this patent is extended or adjusted under 35 U.S.C. 154(b) by 400 days.

(21) Appl. No.: 10/921,045

(22) Filed: Aug. 18, 2004

(65) Prior Publication Data

US 2005/0019415 A1 Jan. 27, 2005

Related U.S. Application Data

(62) Division of application No. 10/053,401, filed on Nov. 9, 2001, now Pat. No. 6,808,715.

(51) Int. Cl.
| | |
|---|---|
| *A61K 9/14* | (2006.01) |
| *A61K 33/06* | (2006.01) |
| *A61K 33/08* | (2006.01) |
| *A61K 33/10* | (2006.01) |
| *A61K 33/34* | (2006.01) |
| *A61K 31/07* | (2006.01) |

(52) U.S. Cl. ............. 424/489; 424/637; 424/687; 424/691; 424/696; 514/725; 514/844

(58) Field of Classification Search .......... 424/489, 424/637, 687, 691, 696; 514/725, 844
See application file for complete search history.

(56) References Cited

U.S. PATENT DOCUMENTS

| | | | |
|---|---|---|---|
| 4,931,284 A | 6/1990 | Ekman et al. | |
| 4,954,532 A | 9/1990 | Elliott et al. | |
| 5,053,222 A | 10/1991 | Takasu et al. | |
| 5,059,414 A | 10/1991 | Dallal et al. | |
| 5,062,994 A | 11/1991 | Imperatori | |
| 5,106,609 A | 4/1992 | Bolich et al. | |
| 5,185,155 A | 2/1993 | Behan et al. | |
| 5,185,325 A | 2/1993 | Brawn et al. | |
| 5,190,747 A | 3/1993 | Sekiguchi et al. | |
| 5,230,835 A | 7/1993 | Deguchi et al. | |
| 5,269,958 A | 12/1993 | de Jager | |
| 5,785,977 A | 7/1998 | Breithbarth | |
| 6,156,804 A | 12/2000 | Chevalier et al. | |
| 6,379,680 B2 * | 4/2002 | Gers-Barlag et al. | ....... 424/401 |
| 6,403,057 B1 | 6/2002 | Schneider et al. | |
| 2003/0007985 A1 | 1/2003 | Chevalier et al. | |

FOREIGN PATENT DOCUMENTS

EP 0 456 460 11/1991

(Continued)

OTHER PUBLICATIONS

Estroff, L. A.; "At the Literal and Figurative Interface of Organic and Inorganic Chemistry: Bio-Inspired Synthesis of Composite Materials;" pp. 1-6; Department of Chemistry, Yale University.

(Continued)

*Primary Examiner*—Johann R. Richter
*Assistant Examiner*—Konata M. George

(57) ABSTRACT

An emulsion comprising: water; hydrophilic particles; and hydrophobic particles; wherein the hydrophilic and hydrophobic particles form shells encapsulating a gas that are suspended in the water, said shells comprising an external layer of hydrophilic particles and an internal layer of hydrophobic particles adjacent to the layer of hydrophilic particles.

31 Claims, 6 Drawing Sheets

FOREIGN PATENT DOCUMENTS

| EP | 0 478 326 | 4/1992 |
|---|---|---|
| EP | 0 288 419 | 7/1992 |
| EP | 0 998 902 | 5/2000 |
| FR | 2 774 906 | 8/1999 |
| WO | WO 92/15284 | 9/1992 |
| WO | WO 98/42301 | * 10/1998 |
| WO | WO 99/40902 | 8/1999 |

OTHER PUBLICATIONS

Duguet, E.; "Sol-gel Chemistry and Engineering Background;" pp. 1-18; Introduction to Hybrid Organic-Inorganic Materials; University Bordeaux.

JP 03-006269 A; Jan. 11, 1991; Yamaguchi, K. & Patent Abstracts of Japan; vol. 015; No. 123 (C-0816); Mar. 26, 1991.

JP 07-138131 A; May 30, 1995; Miyamoto, T. & Patent Abstracts of Japan; vol. 1995; No. 08; Sep. 29, 1995.

JP 08-053512 A; Feb. 27, 1996; Ishii, S. & Patent Abstracts of Japan; vol. 1996; No. 06; Jun. 28, 1996.

Database WPI; Section Ch, Week 200114; Derwent Publications Ltd.; London, GB; AN 2001-127030; XP002233771; & JP 2000-264815 (Shinetsu Chem. Ind. Co. Ltd.) abstract.

* cited by examiner

WRINKLE CREAM

RELATED APPLICATIONS

The present application is a divisional application of U.S. application Ser. No. 10/053,401 filed on Nov. 9, 2001 now U.S. Pat. No. 6,808,715, the disclosure of which is incorporated herein by reference.

FIELD OF THE INVENTION

The invention relates to cosmetic materials and in particular to cosmetic materials used to improve the appearance of skin and reduce skin wrinkles.

BACKGROUND OF THE INVENTION

Numerous cosmetics exist for treatment and concealment of wrinkles. The problem of how to alleviate wrinkling and improve the health and appearance of wrinkled skin is ubiquitous and cosmetic methods for treatment of wrinkles are avidly sought.

U.S. Pat. No. 6,156,804, the disclosure of which is incorporated herein by reference, describes treating wrinkles and fine lines on the skin by topically treating the skin with a microdispersion of wax in a topical composition. U.S. Pat. No. 5,185,155, the disclosure of which is incorporated herein by reference, describes encapsulating hydrophobic material to form a dispersion of micro-encapsulates for use in cosmetic products.

SUMMARY OF THE INVENTION

An aspect of some embodiments of the present invention relates to providing a cosmetic material that reduces wrinkling and improves appearance of skin to which it is applied.

An aspect of some embodiments of the present invention relates to providing a cosmetic substance, which when applied to the skin forms a network of filaments of the cosmetic substance on the skin. The network anchors itself to the skin and to furrows of wrinkles in the skin. As a result of attraction between components of the cosmetic material from which the filaments are formed, the filaments tend to contract with substantial force. The network as a whole therefore tends to contract. Since the filaments of the network are anchored to the skin and furrows of wrinkles therein, the network functions to mechanically "pull out" wrinkle furrows in the skin, thereby smoothing the skin and drawing the skin taut.

An aspect of some embodiments of the present invention relates to providing a cosmetic substance, which when applied to the skin diffuses water by osmosis to blood vessels, interstitial fluid and cells in the skin and causes thereby the structure of the skin to swell and expand. The swelling tends to flatten out wrinkles and improve flow of blood and interstitial fluid in the skin that irrigates the skin with nutrients and removes metabolic waste materials from the skin.

An aspect of some embodiments of the present invention relates to providing a cosmetic substance that provides a peeling effect that detaches dead skin cells from the surface of the epidermis. When the cosmetic substance is removed from the skin, the detached dead skin cells are removed with the cosmetic substance.

In some embodiments of the present invention two or three of the aspects are present.

A cosmetic substance, in accordance with an embodiment of the present invention, comprises a composition of matter formed from water, hydrophilic silica particles and hydrophobic silica particles. In some embodiments of the invention a mass of hydrophilic particles in the composition is substantially greater than a mass of hydrophobic particles in the composition. For example, some embodiments of the present invention, may typically have mass ratios of hydrophilic to hydrophobic particles in a range from 6 to 20. Some embodiments may typically have mass ratios in a range from 3 to 10. Other mass ranges, in accordance with embodiments of the present invention are also possible. In some embodiments of the present invention, the composition takes a form of an aqueous emulsion. A majority of the hydrophilic particles in the emulsion remains in solution in the water and tends to form, with the water, a gel-like structure comprising relatively long filaments of hydrophilic particles to which water molecules adhere. Hydrophobic particles and a relatively small portion of the hydrophilic particles aggregate to form double layer shells that encapsulate pockets of air that are suspended in the water. The hydrophobic particles in a shell that encapsulates an air pocket are concentrated in an inner layer of the shell, which inner layer is in contact with the air in the air pocket. The hydrophilic particles in the shell are concentrated in an outer layer of the shell, which outer layer is in contact with the water. Optionally, additional hydrophilic particles are distributed in the water.

In some embodiments of the present invention, the cosmetic substance is powder-like and hereinafter is referred to as a powder. Particles that form the powder are droplets of water with hydrophilic particles in solution, each droplet encapsulated in a double layer shell having an inner layer comprising hydrophilic particles and an outer layer comprising hydrophobic particles. Most of the hydrophilic particles in the powder are dispersed in the water in the encapsulated water droplets and, as in the emulsion form of the cosmetic composition, tend to form with the water a gel-like structure comprising filaments of hydrophilic particles adhered with water molecules.

When the cosmetic substance, in either the emulsion or powder form, is rubbed into a region of skin, it forms a layer of the cosmetic substance on the surface of the skin. A portion of the hydrophilic particles in the layer migrate to and enter sweat gland ducts in the skin region, forming tendrils of hydrophilic particles that penetrate into the ducts. A portion of the hydrophobic particles migrate to and enter ducts of sebaceous glands located in hair follicles in the skin region, forming tendrils of hydrophobic particles that protrude into the hair follicles and ducts of their sebaceous glands. In particular, the hydrophilic and hydrophobic tendrils protrude into hair follicles and ducts of sweat glands and sebaceous glands in furrows of wrinkles in the skin region. Water in the cosmetic material diffuses by osmoses into interstitial fluid and cells in the skin.

As water leaves the cosmetic substance, the volume of the cosmetic substance contracts and the layer shrinks to a network of filaments on the skin. Each of the filaments is formed from a slurry of hydrophilic and hydrophobic particles in water. The hydrophilic and hydrophobic tendrils anchor the filaments to the skin region and wrinkle furrows therein.

As a result of the attraction of the hydrophilic particles to water and attraction of the hydrophobic particles to the hydrophilic particles and to water, the filaments tend to contract aggressively. It is noted that hydrophobic molecules do not generally repel water and are often attracted to water with greater force than they are attracted to each other.

Hydrophobic effects evidenced by hydrophobic molecules generally result from attraction of water molecules to each other being greater than attraction of water to the hydrophobic molecules. The cosmetic filamentary network therefore tends to contract aggressively and thereby pulls out furrows of wrinkles in the skin and smoothes the skin.

The cosmetic substance optionally also functions as a peeling agent that tends to peel off dead skin cells from the epidermis. As a result of capillary action and attraction of hydrophilic and hydrophobic particles in the cosmetic substance to moisture and natural oils in the skin respectively, water and hydrophilic and/or hydrophobic particles in the cosmetic tend to penetrate between dead skin cells and the surface of the epidermis. If the skin is wet or moist, water and predominantly hydrophilic particles will tend to penetrate and concentrate between the dead skin cells and the epidermis. If the skin is oily, water and predominantly hydrophobic particles will tend to penetrate and concentrate between the dead skin cells and the epidermis. If the dead skin cells are dry, water in the cosmetic will tend to be absorbed by the dead skin cells resulting in their swelling. The penetration and concentration of the hydrophobic and/or hydrophilic between dead skin cells and the epidermis tends to pry up and dislodge the dead skin cells from the epidermis. Swelling of dry dead skin cells also tends to mechanically dislodge the dead skin cells from the epidermis. When the cosmetic substance is removed from the skin, the dislodged dead skin cells are removed with the cosmetic substance.

There is therefore provided in accordance with an embodiment of the present invention, an emulsion comprising: water; hydrophilic particles; and hydrophobic particles; wherein the hydrophilic and hydrophobic particles form shells encapsulating a gas that are suspended in the water, said shells comprising an external layer of hydrophilic particles and an internal layer of hydrophobic particles adjacent to the layer of hydrophilic particles. Optionally, hydrophilic particles are dispersed in the water and form with the water a gel-like structure having filaments of hydrophilic particles to which water molecules adhere.

In some embodiments of the present invention, the shells have a characteristic diameter in a range from about 1 micrometer to about 20 micrometers.

In some embodiments of the present invention, a relative concentration by weight of the hydrophobic particles in the emulsion is such that the emulsion does not tend to become a powder.

In some embodiments of the present invention, a concentration by weight of hydrophobic particles in the emulsion is between 0.5% and 1.8%.

In some embodiments of the present invention, hydrophobic particles have a characteristic specific surface greater than about 100 $m^2/g$.

In some embodiments of the present invention, a relative concentration by weight of the hydrophilic particles in the emulsion is about equal to $K_{phil}/S_{phil}$ where $S_{phil}$ is a characteristic specific surface of the hydrophilic particles and $K_{phil}$ is a constant having a value between about 20 $m^2/g$ and about 50 $m^2/g$. Optionally, Kphil has a value between about 30 $m^2/g$ and about 40 $m^2/g$.

In some embodiments of the present invention, the hydrophilic particles have a characteristic specific surface greater than about 100 $m^2/g$.

In some embodiments of the present invention, a characteristic diameter of the hydrophilic particles is between about 5 nm and about 150 nm.

In some embodiments of the present invention, the hydrophilic particles comprise oxide particles having surfaces covered with polar radicals. Optionally, the hydrophilic particles comprise a mix of hydrophilic particles, said mix comprising a first type of hydrophilic particles formed from particles based on a first oxide and at least one second type of hydrophilic particles formed from particles based on a second oxide different from the first oxide. Optionally, the polar radicals are selected from the group consisting of OH, $CA_2CO_3$, $CUSO_4$ and $CASO_4$.

In some embodiments of the present invention, the hydrophobic particles comprise oxide particles having surfaces covered with non-polar radicals. Optionally, An emulsion according to claim 20 wherein the hydrophobic particles comprises a mix of hydrophobic particles, said mix comprising a first type of hydrophobic particles formed from particles based on a first oxide and at least one second type of hydrophobic particles formed from particles based on a second oxide different from the first oxide.

In some embodiments of the present invention, the oxide particles are selected from the group consisting of $SiO_2$, $Al_2O_3$, $TiO_2$, $Fe_2O_3$ and MnO particles.

In some embodiments of the present invention, the gas is air.

In some embodiments of the present invention, the gas is ozone.

In some embodiments of the present invention, a substance beneficial for skin care is present in the water. Optionally, the substance is an oil. Optionally, the substance is vitamin A. Optionally, the substance is beta carotine.

There is further provided, in accordance with an embodiment of the present invention, a powder comprising: water; hydrophilic particles; and hydrophobic particles; wherein the water is encapsulated in shells comprising an external layer of hydrophobic particles and an internal layer of hydrophilic particles adjacent to the layer of hydrophobic particles. Optionally, hydrophilic particles are dispersed in solution in the encapsulated water and form with the water a gel-like structure having filaments of hydrophilic particles to which water molecules adhere.

In some embodiments of the present invention, the hydrophobic particles have a characteristic specific surface greater than about 100 $m^2/g$.

In some embodiments of the present invention, a relative concentration $C_{phil}$ by weight of the hydrophilic particles in the powder satisfies an equation $C_{phil}=K_{phil}/S_{phil}$ where $S_{phil}$ is a characteristic specific surface of the hydrophilic particles and $K_{phil}$ is a constant having a value between about 20 $m^2/g$ and about 50 $m^2/g$. Optionally, $K_{phil}$ has a value between about 30 $m^2/g$ and about 40 $m^2/g$.

In some embodiments of the present invention, the hydrophilic particles have a specific surface greater than about 100 $m^2/g$.

In some embodiments of the present invention, a characteristic diameter of hydrophilic particles is between about 5 nm and about 150 nm.

In some embodiments of the present invention, the shells have a characteristic average diameter in a range from about 1 micrometer to about 20 micrometers.

In some embodiments of the present invention, the hydrophilic particles comprise oxide particles having surfaces covered with non-polar radicals. Optionally, the hydrophilic particles comprise a mix of hydrophilic particles, said mix comprising a first type of hydrophilic particles formed from particles based on a first oxide and at least one second type of hydrophilic particles formed from particles based on a second oxide different from the first oxide. Optionally, the polar radicals are selected from the group consisting of OH, $CA_2CO_3$, $CUSO_4$ and $CASO_4$.

In some embodiments of the present invention, the hydrophobic particles comprise oxide particles having surfaces covered with non-polar radicals. Optionally, the hydrophobic particles comprises a mix of hydrophobic particles, said mix comprising a first type of hydrophobic particles formed from particles based on a first oxide and at least one second type of hydrophobic particles formed from particles based on a second oxide different from the first oxide.

In some embodiments of the present invention, the oxide particles are selected from the group consisting of $SiO_2$, $Al_2O_3$, $TiO_2$, $Fe_2O_3$ or MnO particles.

In some embodiments of the present invention, a substance beneficial for skin care is present in the water. Optionally, the substance is an oil. Optionally, the substance is vitamin A. Optionally, the substance is beta carotine.

There is also provided, in accordance with an embodiment of the present invention, a method of reducing wrinkling in a region of skin comprising: forming a layer of an emulsion according to an embodiment of the present invention on the region; and waiting a sufficient period of time so that a portion of the water from the emulsion is absorbed by the region and the volume of the layer shrinks so that the layer transforms into a network of strands on the region, which network is anchored to the skin by attraction of hydrophilic and hydrophobic particles to the skin and tends to contract as water is absorbed from the emulsion.

In some embodiments of the present invention, the method comprises applying water to the region of skin after the network is formed so that the network absorbs water and expands and subsequently releases water to the skin and contracts again.

In some embodiments of the present invention, the method comprises applying a substance comprising a component that is absorbed by the network and the skin to the region of skin after the network is formed so that the network absorbs the component and expands and subsequently releases the component to the skin and contracts again. Optionally, the component is an oil. Optionally, the component is vitamin A. Optionally, the component is beta carotine.

There is further provided in accordance with an embodiment of the present invention, A method of reducing wrinkling in a region of skin comprising: applying a powder in accordance with an embodiment of the present invention to the region so that shells in the powder rupture and release their water content and the released water, hydrophilic particles and hydrophobic particles in the ruptured cells form a layer on the region; and waiting a sufficient period of time so that at least portion of water in the layer is absorbed by the region and the volume of the layer shrinks so that the layer transforms into a network of strands on the region, which network is anchored to the skin by attraction of hydrophilic and hydrophobic particles to the skin and tends to contract as water is absorbed from the network.

In some embodiments of the present invention, the method comprises applying water to the region of skin after the network is formed so that the network absorbs water and expands and subsequently releases water to the skin and contracts again.

In some embodiments of the present invention, the method comprises applying a substance comprising a component that is absorbed by the network and the skin to the region of skin after the network is formed so that the network absorbs the component and expands and subsequently releases the component to the skin and contracts again. Optionally, the component is an oil. Optionally, the component is vitamin A. Optionally, the component is beta carotine.

There is further provided, in accordance with an embodiment of the present invention, A method of forming an aqueous emulsion in which encapsulated pockets of gas are suspended in water comprising: forming a solution of water and hydrophilic particles; adding a quantity of hydrophobic particles to the solution to form a mixture; causing the gas to be present in the mixture while causing the gas to cavitate so as to generate pockets of the gas in the mixture and wherein the quantity of hydrophobic particles added to the mixture is not sufficient to cause the cavitating mixture to form a powder.

There is further provided, in accordance with an embodiment of the present invention, a method of forming a powder comprising water, the method comprising: forming a solution of water and hydrophilic particles; adding a quantity of hydrophobic particles to the solution to form a mixture; causing the gas to cavitate so that droplets of the water are encapsulated in shells of hydrophilic and hydrophobic particles and wherein the amounts of hydrophobic and hydrophilic particles in the mixture are enough to form a sufficient number of shells so that substantially all the water in the mixture can be contained in encapsulated water droplets.

BRIEF DESCRIPTION OF FIGURES

Non-limiting examples of embodiments of the present invention are described below with reference to figures attached hereto. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale. The figures are listed below.

DETAILED DESCRIPTION OF EXEMPLARY EMBODIMENTS

Figure 1A:
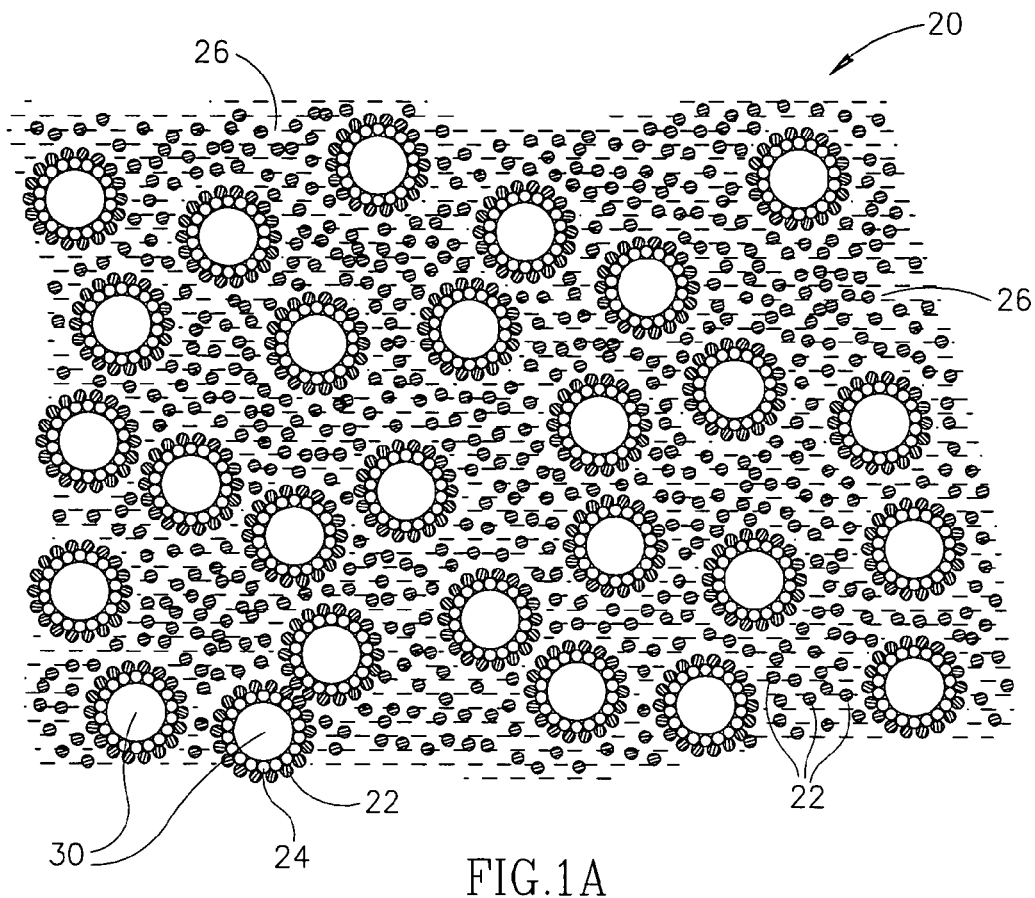
FIGS. 1A and 1B schematically show a cosmetic emulsion and details of its composition, in accordance with an embodiment of the present invention.

FIG. 1A schematically shows a cosmetic aqueous emulsion 20, in accordance with an embodiment of the present invention. Cosmetic emulsion 20 comprises hydrophilic particles represented schematically by shaded circles 22 and hydrophobic particles represented by unshaded circles 24 suspended in water 26. A number of hydrophilic particles 22 in emulsion 20 is optionally substantiality greater than a number of hydrophobic particles 24 in the emulsion.

A hydrophilic particle 22, in accordance with an embodiment of the present invention, may be formed from an oxide particle which has its surface covered with polar radicals. Any of a large variety of different oxides may be used to form a hydrophilic particle, for example a hydrophilic particle may be formed from a silica ($SiO_2$), alumina ($Al_2O_3$), titanium oxide $TiO_2$, $Fe_2O_3$ or MnO particle having its surface covered with polar radicals. The polar radicals are, preferably, hydroxyl radicals (i.e. OH), though other polar radicals such as $Ca_2CO_3$, $CuSO_4$, $CaSO_4$ may also be used. A hydrophobic particle 24, in accordance with an embodiment of the present invention, may be formed from an oxide particle having its surface covered with non-polar radicals, such as for example methyl radicals (i.e. $CH_3$). As in the case of a hydrophilic particle 22, a hydrophobic particle 24 may be based on any one of a large variety of different oxide particles.

Hydrophilic particles 22 in emulsion 20, in accordance with an embodiment of the present invention, may comprise hydrophilic particles of a same type, i.e. all based on a same type oxide particle, or a mix of different types of hydrophilic particles, in which each type is based on a different type oxide particle. Similarly, hydrophobic particles 24 in emulsion 20 may comprise a single type of hydrophobic particle based on a same type oxide particle, or comprise hydrophobic particles of different types.

Figure 1B:
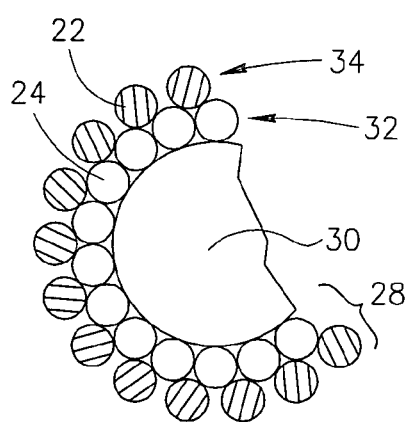

Hydrophobic particles 24 and a relatively small portion of hydrophilic particles 22 aggregate to form double layer shells 28 that encapsulate pockets of air 30, which are suspended in water 26. A large proportion of hydrophilic particles 22 remains dispersed in water 26, as is schematically shown in FIG. 1A. Details of structure of shells 28 that encapsulate air pockets 30 are shown in an enlarged, partially cutaway schematic of a shell 28 in FIG. 1B. An inner layer 32 of each shell 28 comprises hydrophobic particles 24 and an outer layer 34 of the shell comprises hydrophilic particles 22. Whereas for simplicity of presentation, inner layer 32 of hydrophobic particles 24 is shown as a single layer of hydrophobic particles 24, inner layer 32 may comprise a small plurality of layers of hydrophobic particles. Similarly, outer layer 34, which is shown comprising a single layer of hydrophilic particles 22, may comprise a plurality of layers of hydrophilic particles. For hydrophilic particles 22 having a same size as hydrophobic particles 24, generally, the number of hydrophilic particles 22 in shell 28 is about equal to the number and hydrophobic particles 24 in the shell.

Hydrophilic particles 22 and hydrophobic particles 24 preferably have a specific surface (i.e. surface to mass ratio) that is greater than about 100 $m^2/g$ and preferably substantially greater. It is advantageous for hydrophilic and hydrophobic particles 22 and 24 to be as small as possible and to the extent that the specific surface of a particle is greater, the size of the particle is smaller. To the extent that the particles are smaller, the size of air pockets 30 tend to be smaller and a larger fraction of the total surface area of shells 28 encapsulating air pockets 30 contacts and interacts directly with the skin when cosmetic emulsion 20 is applied to the skin. Contact with the skin of a shell 28 of an air pocket 30 tends to rupture the shell, freeing hydrophilic and hydrophobic particles 22 and 24 in the shell to contact and interact with the skin. In addition, the smaller the size of hydrophilic particles 22 and hydrophobic particles 24, the more easily do the particles flow into ducts of sweat glands and sebaceous glands in the skin, as described below.

It noted however, that hydrophilic and hydrophobic particles 22 and 24 should not be too small. As the size of hydrophilic and hydrophobic particles 22 and 24 is reduced and air pockets 30 become smaller, hydrophilic and hydrophobic particles 22 and 24 in shells 28 of the air pockets are more tightly bound to each other. It therefore becomes more difficult to rupture shells 28 and free hydrophilic and hydrophobic particles 22 and 24 that they comprise. As a result, activity of cosmetic emulsion 20 is restrained and its cosmetic efficacy reduced. Advantageously, diameters of air pockets 30 range from about 1 micrometer to about 20 micrometers. For air pockets 30 having diameters substantially smaller that about 1 micrometer, shells 28 of the air pockets are generally not ruptured easily enough. Air pockets 30 having diameters greater than about 20 micrometers are generally mechanically unstable. Diameters of hydrophilic and hydrophobic particles 22 and 24 range correspondingly from about 5 nm to about 150 nm.

Hydrophilic and hydrophobic silica particles having average specific surfaces in the ranges from about 100 $m^2/g$ to about 400 $m^2/g$ and from about 100 $m^2/g$ to about 280 $m^2/g$. respectively are currently available commercially. For example, Degussa of Germany markets hydrophilic and hydrophobic particles having specific surfaces in the above noted range under the brand name AEROSIL. Cabot of the US also markets hydrophilic and hydrophobic silica particles that have specific surfaces in the above noted ranges under the brand name CAB-O-SIL. For the above noted specific surfaces, hydrophilic and hydrophobic particles in the commercially available products have diameters in a range from about 5 nm to about 150 nm.

Concentration of hydrophobic particles 24 in emulsion 20 controls an amount of air encapsulated in the emulsion and thereby the amount of water 26 per unit volume of the emulsion. As the amount of hydrophobic particles 24 in emulsion 20 increases, the amount of air trapped in the emulsion increases and the amount of water 26 per cubic centimeter of emulsion decreases. The inventors have determined that water content of emulsion 20 is advantageously between about 40% and about 70% by volume. Though water content of emulsion 20 can be less than 40% and greater than 70%, for water content less than 40% the emulsion tends to be too dry and for water content above 70% the emulsion tends to be too watery. The advantageous water content range corresponds to a concentration of hydrophobic particles 24 in emulsion 20 in a range from about 0.5% to about 1.5% by weight.

The concentration of hydrophobic particles 24 in emulsion 20 must generally be below a certain threshold concentration, hereinafter referred to as a "powder threshold". Concentrations of hydrophobic particles greater than the powder threshold are generally not possible for the emulsion form of a cosmetic composition in accordance with an embodiment of the present invention and are characteristic of the powder form of a cosmetic composition in accordance with an embodiment of the present invention. Let $C_{phob}$ represent the relative concentration (not percent) by weight of hydrophobic particles 24 in emulsion 20. The inventor has found that to maintain integrity and stability of emulsion 20 as an emulsion, concentration, $C_{phob}$ should satisfy a relation $C_{phob} \leq K_{phob}/S_{phob}$, where $S_{phob}$ is a characteristic specific surface of the hydrophobic particles and $K_{phob}$ is a constant. For an emulsion, in accordance with an embodiment of the present invention, similar to emulsion 20, for which hydrophilic and hydrophobic particles 22 and 24 are hydrophilic and hydrophobic silica particles, for which $S_{phob} \cong 260\ m^2/g$, and for substantially pure water, $K_{phob}$ has a value between about 4 $m^2/g$ and about 5 $m^2/g$.

Concentration of hydrophilic particles in emulsion 20 determines viscosity of the emulsion and stability of the emulsion against deterioration by phase separation of its components. The inventor has determined that, in accordance with an embodiment of the present invention, the relative concentration by weight, "$C_{phil}$", of the hydrophilic particles advantageously satisfies an equation $C_{phil} = K_{phil}/S_{phil}$. In the equation for $C_{phil}$, $S_{phil}$ is a specific surface of hydrophilic particles 22 and $K_{phil}$ is a constant. The inventor has determined that for hydrophilic silica particles having $S_{phil} \cong 380$ m$^2$/g, $K_{phil}$ less than about 20 m$^2$/g emulsion 20 is generally too watery, while for $K_{phil}$ greater than about 40 m$^2$/g, the emulsion becomes very viscous and paste-like. Whereas, both a watery and a paste-like form of emulsion 20 can be advantageous, generally a value for $K_{phil}$ between about 20 m$^2$/g and 40 m$^2$/g is advisable. For a range for values for $K_{phil}$ between about 20 m$^2$/g and about 40 m$^2$/g, concentration by weight of hydrophilic particles 22 in emulsion 20 ranges from about 7% to about 11%.

The inventor has determined that different values of pH for cosmetic emulsions similar to emulsion 20 are advantageous for different skin types. For example, for normal skin that is neither too oily nor too dry, a pH between 5.2 and 5.5 can be advantageous. For oily skin, a pH about equal to 4 can be advantageous. The pH of emulsion 20 is determined by relative concentrations of hydrophilic particles 22 and hydrophobic particles 24 and/or by addition of appropriate ions, such as silver ions. Generally, if an ion is added to emulsion 20, the ion concentration is a dominant factor in determining the pH of the emulsion.

To provide an example of how to produce an emulsion in accordance with an embodiment of the present invention similar to emulsion 20, assume that it is desired to produce a kilogram of the emulsion and that particles 22 and 24 are hydrophilic and hydrophobic silica particles respectively. Assume that the specific surfaces of hydrophilic particles 22 is 380 m$^2$/g and that $K_{phil}=38$ m$^2$/g so that the concentration $C_{phil}$ of hydrophilic particles by weight is about 0.1. Assume that $S_{phob} \cong 380$ m$^2$/g and for a desired concentration of water 26 in emulsion 20 that concentration $C_{phob}$ of hydrophobic particles 24 should be about 0.01. Then, a kilogram of emulsion 20 should comprise about 10 g of hydrophobic particles 24 and about 100 g of hydrophilic particles 22. A remainder of emulsion 20, about 890 g, is highly purified water optionally having substances, for example vitamins or an antiseptic agent, beneficial for skin care dissolved or dispersed therein.

To produce emulsion 20, 890 g of water and 100 g of hydrophilic particles 22 are mixed together for five to ten minutes in a DS-CH4000RM mixer sold by Shiangtai Machinery Industry of Japan having a 50 mm propeller rotating at about 500 rpm. Following mixing at 500 rpm, mixing continues for 10-15 minutes at about 1000 rpm and then for an additional period of 75-80 minutes at between about to about 2500 rpm. At the end of the additional mixing period of 75-80 minutes, 10 g of hydrophobic particles 24 are added to the mixture and the mixture is mixed for about 30 minutes at a mixing speed of about 1000 to about 1500 RPM. The mixing is then stopped and the resultant mixture of hydrophilic particles 22, hydrophobic particles 24 and water is set aside for a period of about 24 hours, during which it is maintained at a constant temperature of about 20° C. and isolated from mechanical vibration and shock. During this "quiet" period extraneous gas bubbles introduced into the mixture during mixing are released and the mixture gels and matures into the emulsion.

It is noted that whereas FIG. 1 shows shells 28 in emulsion 20 encapsulating air pockets 30, in accordance with an embodiment of the present invention, a formulation similar to emulsion 20 can be produced in which shells 28 encapsulate a gas or mixture of gases other than air. For example, a cosmetic formulation, in accordance with an embodiment of the present invention, can be formed in which shells 28 encapsulate ozone or some other gas or gas mixture that is beneficial for skin care. During manufacture of the emulsion a given desired gas or gas mixture is encapsulated in the emulsion, in accordance with an embodiment of the present invention, by bubbling or otherwise suffusing the mixture of water and particles from which the emulsion is being formed with the gas.

Figure 2A:
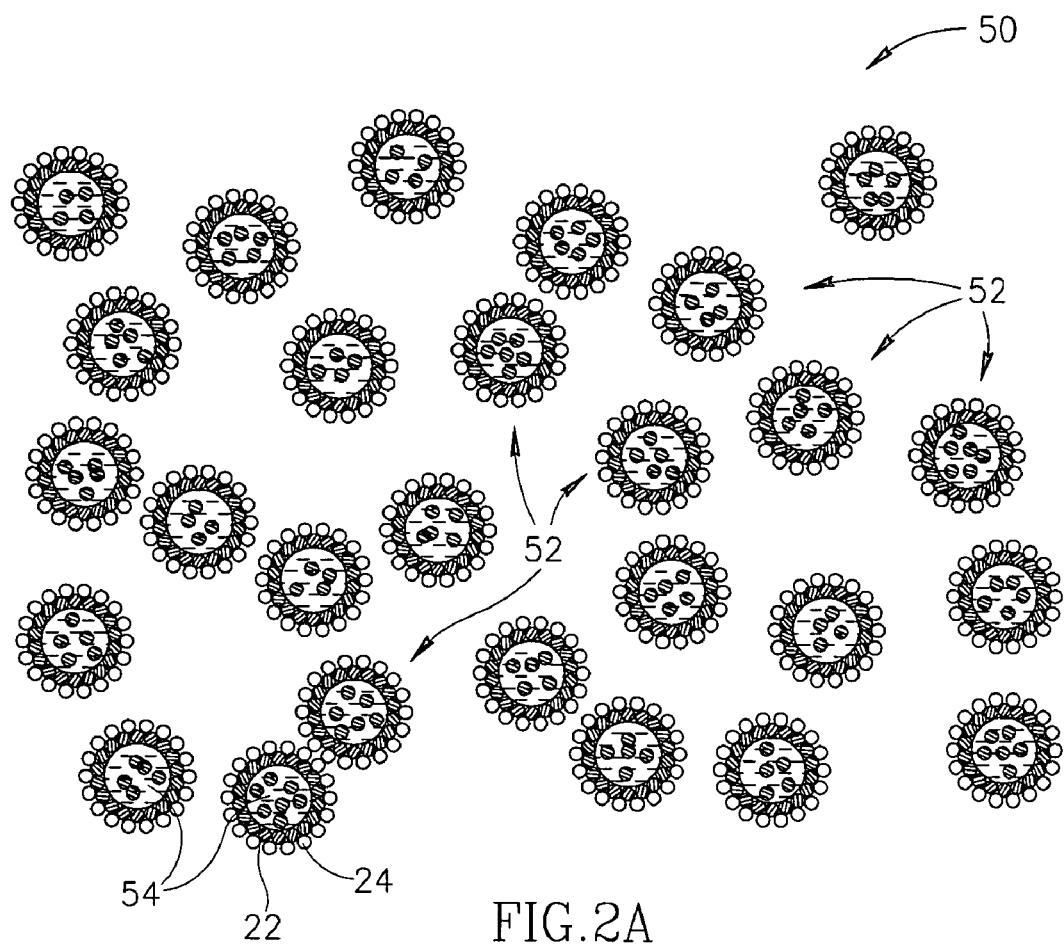
FIGS. 2A and 2B schematically show a cosmetic powder and details of its composition, in accordance with an embodiment of the present invention.
Figure 2B:
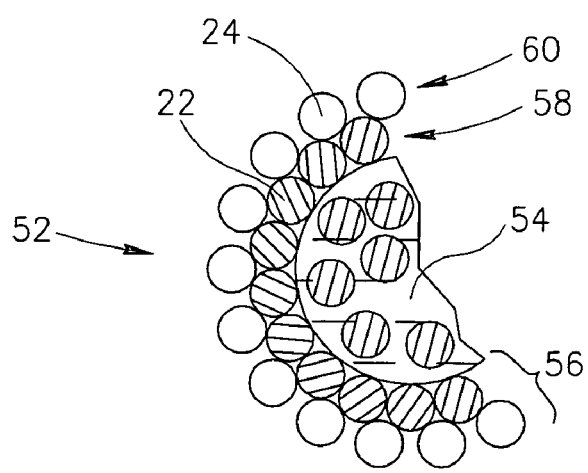

FIG. 2A schematically shows a cosmetic powder 50, in accordance with an embodiment of the present invention. Cosmetic powder 50 comprises powder particles 52 each particle of which comprises a droplet of water 54 encapsulated in a double layer shell 56 of hydrophilic and hydrophobic silica particles 22 and 24. Hydrophilic particles 22 form an inner layer 58 of shell 56 and hydrophobic particles 24 form an outer layer 60 of the shell. Hydrophilic particles 22 in solution in a water droplet 54 optionally, form with the water in the droplet a gel-structure comprising relatively long filaments (not shown) of hydrophilic particles to which water molecules are intimately adhered. Some details of structure of powder particles 52 are shown in an enlarged schematic, partial cutaway of a particle 52 in FIG. 2B.

Cosmetic powder 50 is produced similarly to the way in which emulsion 20 is produced by adding hydrophilic and hydrophobic particles 22 and 24 to water and mixing. A main factor in determining if the mixture becomes a cosmetic emulsion or a cosmetic powder, in accordance with an embodiment of the present invention, is an amount of hydrophobic particles 24 added to the water to make the mixture. As noted above, if the concentration of hydrophobic particles 24 is greater than a hydrophobic powder threshold for the mixture, the mixture will form a powder. For example, assume that the hydrophobic and hydrophilic particles 22 and 24 are hydrophobic and hydrophilic silica having specific surfaces respectively the same as the specific surfaces of the hydrophilic and hydrophobic particles used in the above example of formation of emulsion 20. Then if $C_{phob} \geqq K_{phob}/S_{phob}$, where $K_{phob}$ has a value between about 4 m$^2$/g and about 5 m$^2$/g, the mixture will tend to form a powder. For such a concentration of hydrophobic particles, the mixture has enough hydrophobic particles to form surfaces of a sufficient number of shells 56 so that substantially all the water in the mixture is contained in encapsulated water droplets 54.

By way of example, assume that a kilogram of a cosmetic powder similar to cosmetic powder 50 is to be formed, in accordance with an embodiment of the present invention, from hydrophilic and hydrophobic particles having the specific surfaces noted in the example described above for manufacturing cosmetic emulsion 20. Further assume that $K_{phob}$ is equal to about 4.5 m$^2$/g. To form the cosmetic powder, 882 g of water and about 100 g of hydrophilic particles 22 are mixed together for five to ten minutes in a DS-CH4000RM mixer having a 50 mm propeller rotating at about 500 rpm. Following mixing at 500 rpm, mixing continues for 10-15 minutes at about 1000 rpm and then for an additional period of 75-80 minutes at about 2500 rpm. At the end of the additional mixing period of 75-80 minutes, 18 g of hydrophobic particles are added to the mixture. The amount of hydrophobic silica added to the water is such that $C_{phob} \geqq K_{phob}/S_{phob}$, i.e. 18 g>1000 g (4.5 m$^2$/g)/(280 m$^2$/g)$\cong$16. As a result, the mixture can be processed to produce a cosmetic powder rather than a cosmetic emulsion. Following addition of the hydrophobic particles the mixture is mixed for about 30 minutes at a mixing speed of about 3000 RPM. (The mixing speed for the powder is optionally substantially greater than the mixing speed of the emulsion in this stage of the manufacturing process.) The mixing is then stopped and the resultant mixture of hydrophilic silica particles 22, hydrophobic silica particles 24 and water is set aside for a period of about 24 hours during which it is maintained at a constant temperature of about 20° C. and isolated from mechanical vibration and shock. During this 24-hour period the mixture becomes a powder.

It is noted that a cosmetic powder, in accordance with an embodiment of the present invention, similar to powder 50 can be produced in which the water encapsulated by shells 58 contains desired substances, such as vitamins and anti-aging compounds, beneficial to skin care. The substances are added to the water used in producing the powder prior to adding the hydrophilic particles to the water in the process of producing the powder. The added substances will generally change a powder threshold concentration of hydrophobic particles required to produce a stable cosmetic powder in accordance with an embodiment of the present invention.

An emulsion or powder, in accordance with an embodiment of the present invention, corresponding to an emulsion or powder comprising hydrophilic and hydrophobic silica particles can, as noted above, be formed from hydrophilic and hydrophobic particles based on oxides other than silica or on a mix of oxides. Quantities of the "other or mixed oxide" hydrophobic and hydrophilic particles in the corresponding emulsion or powder are quantities that provide substantially same total surface areas as surface areas provided by the quantities of hydrophilic and hydrophobic particles respectively comprised in the silica based emulsion or powder. Cosmetic emulsions and powders for which total surface areas of the other or mixed oxide hydrophobic and hydrophilic particles are different from total surface areas of the silica based hydrophilic and hydrophobic particles may also be formed, in accordance with embodiments of the present invention.

FIGS. 3A-3D schematically show functioning of cosmetic emulsion 20 to improve appearance and relieve wrinkling in a region of skin 70 to which the emulsion is applied, in accordance with an embodiment of the present invention.

Figure 3A:
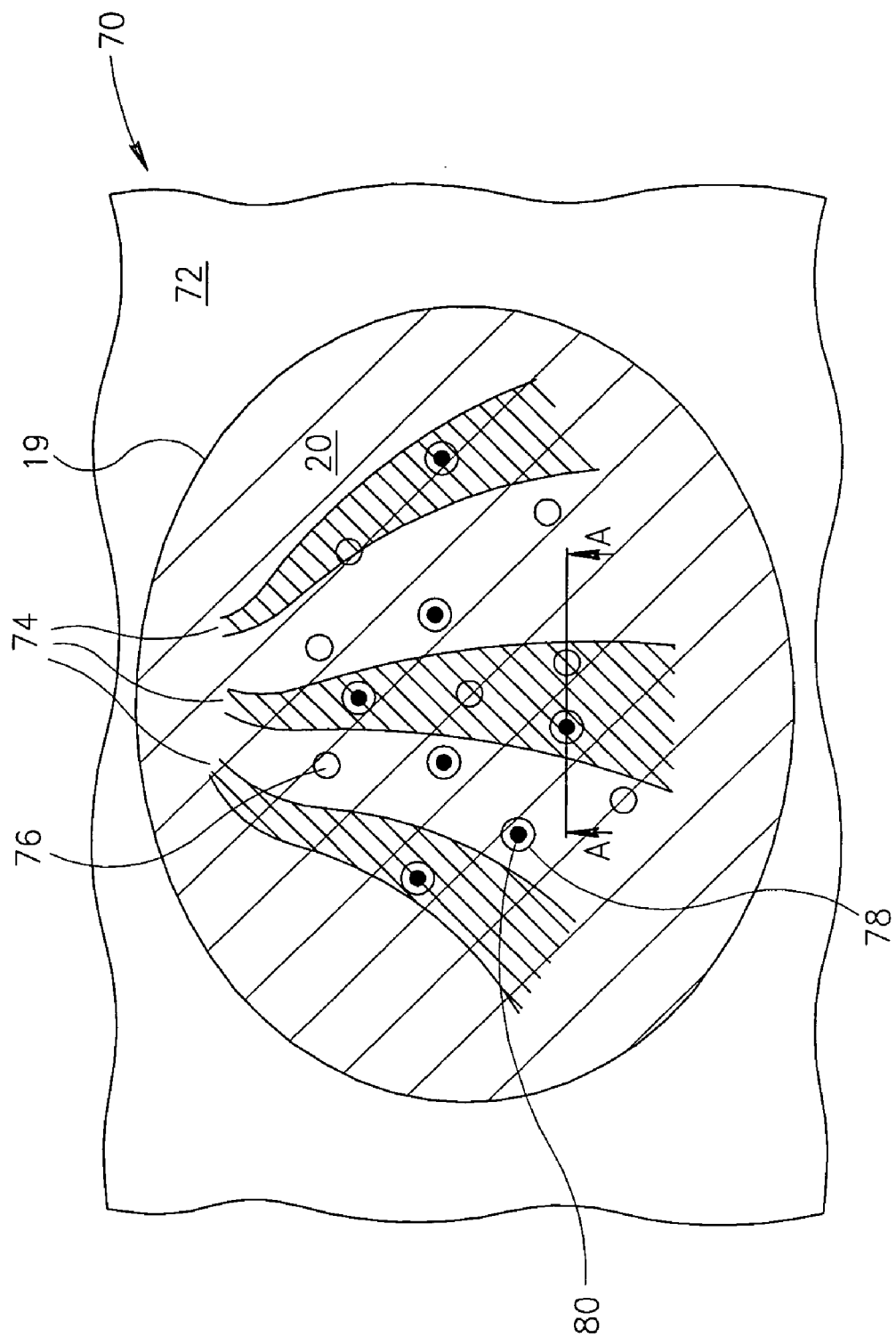
FIGS. 3A-3D schematically illustrate functioning of the cosmetic emulsion shown in FIG. 1 in ameliorating wrinkles in a region of skin to which the emulsion is applied, in accordance with an embodiment of the present invention.

FIG. 3A schematically shows cosmetic emulsion 20 and skin 70 to which the emulsion is applied in a plan view when the emulsion is first applied to the skin. The region of skin 70 has wrinkle furrows indicated by shaded bands 74, sweat gland ducts 76 and hair follicles 78 in which hairs 80 are located. Cosmetic emulsion 20 is applied to the region of skin 70 so that the emulsion forms a thin layer on the region indicated by a shaded area 19. In accordance with an embodiment of the present invention, layer 19 of emulsion 20 is left on the skin for an application period of from about 3 to about 10 minutes.

Figure 3B:
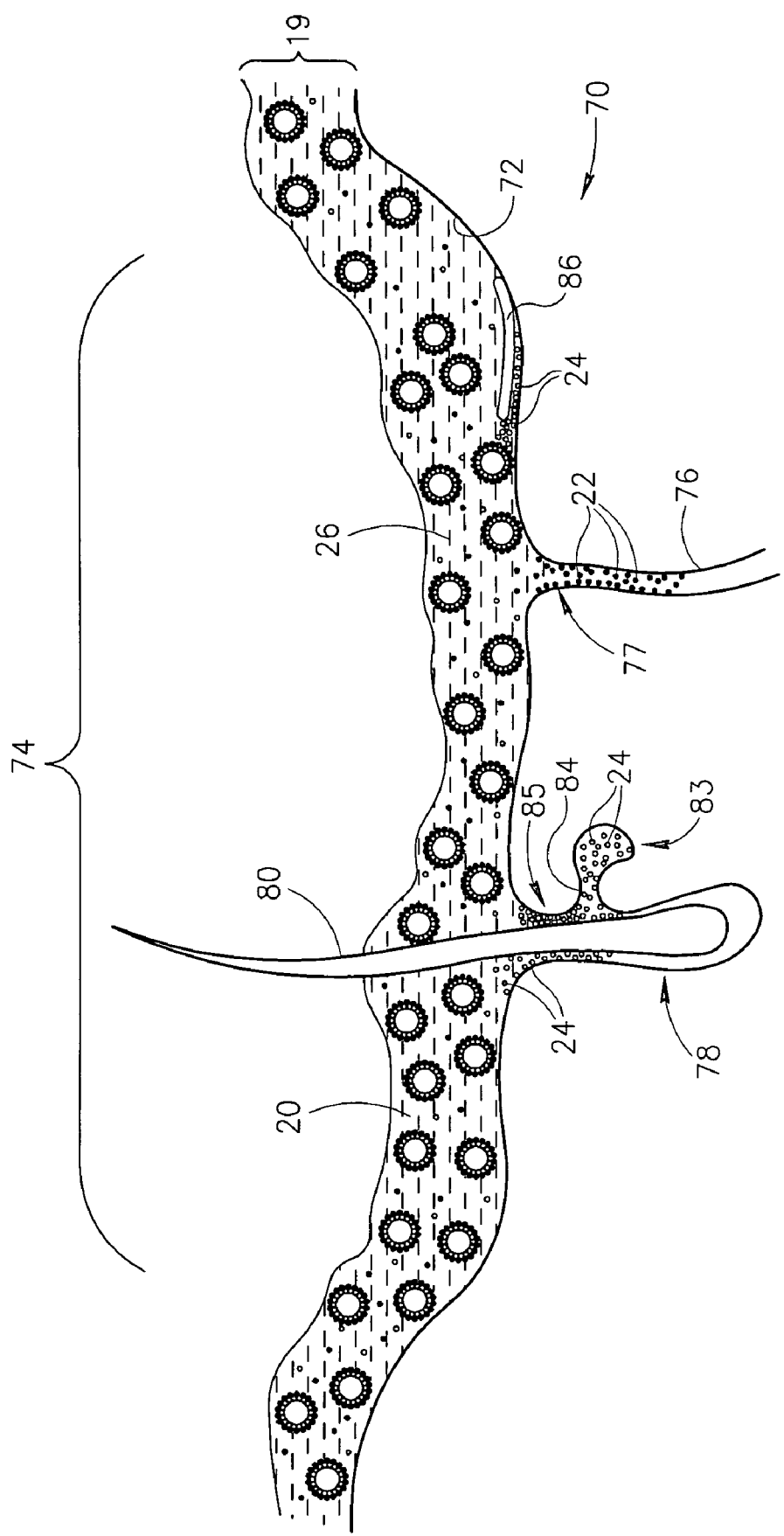

FIG. 3B shows a cross-sectional view along a line A-A of layer 19 of cosmetic emulsion 20 and the region of skin 70 on which the emulsion is located shown in FIG. 3A. The cross sectional view shows a surface 72 of skin 70 and a wrinkle furrow 74 in the surface, in which a sweat gland duct 76 and a hair follicle 78 are located. A hair 80 is located in hair follicle 78 and the hair follicle has a sebaceous gland 83 having a duct 84. A dead skin cell 86 to the right of sweat gland duct 76 adheres to surface 72 of skin 70.

Hydrophilic particles 22 from emulsion 20 migrate to and enter sweat gland duct 76 and form a tendril 77 of hydrophilic particles in the sweat gland duct as a result of the relatively high concentration of water in the duct. Hydrophobic particles 24 migrate to hair follicle 78 and enter into sebaceous gland duct 84 forming a tendril 85 of the hydrophobic particles in the hair follicle and duct as a result of the relatively high concentration of natural body oil in the duct and hair follicle. Hydrophilic and hydrophobic tendrils 77 and 85 and similar tendrils in other regions (not shown) of skin 70 attach emulsion layer 19 to the skin.

Water and hydrophobic particles 24 also tend to concentrate between dead skin cell 86 and surface 72 of skin 70 as a result of capillary action and a relatively high concentration of oil that covers the dead skin cell. The hydrophobic particles 24 between dead skin cell 86 and skin surface 72 tend to "pry up" and dislodge the dead skin cell from the skin surface. Water 26 in emulsion 20, which contacts skin 70, tends to diffuse into cells, blood vessels and interstitial fluid (not shown) in the skin and swell the cells and blood vessels and increase volume of the interstitial fluid. The swelling of the cells and blood vessels and expansion of the interstitial fluid tends to puff out wrinkle furrows 74. However, as a result of loss of water from cosmetic layer 19 to skin 70, volume of the cosmetic emulsion layer shrinks.

Figure 3C:
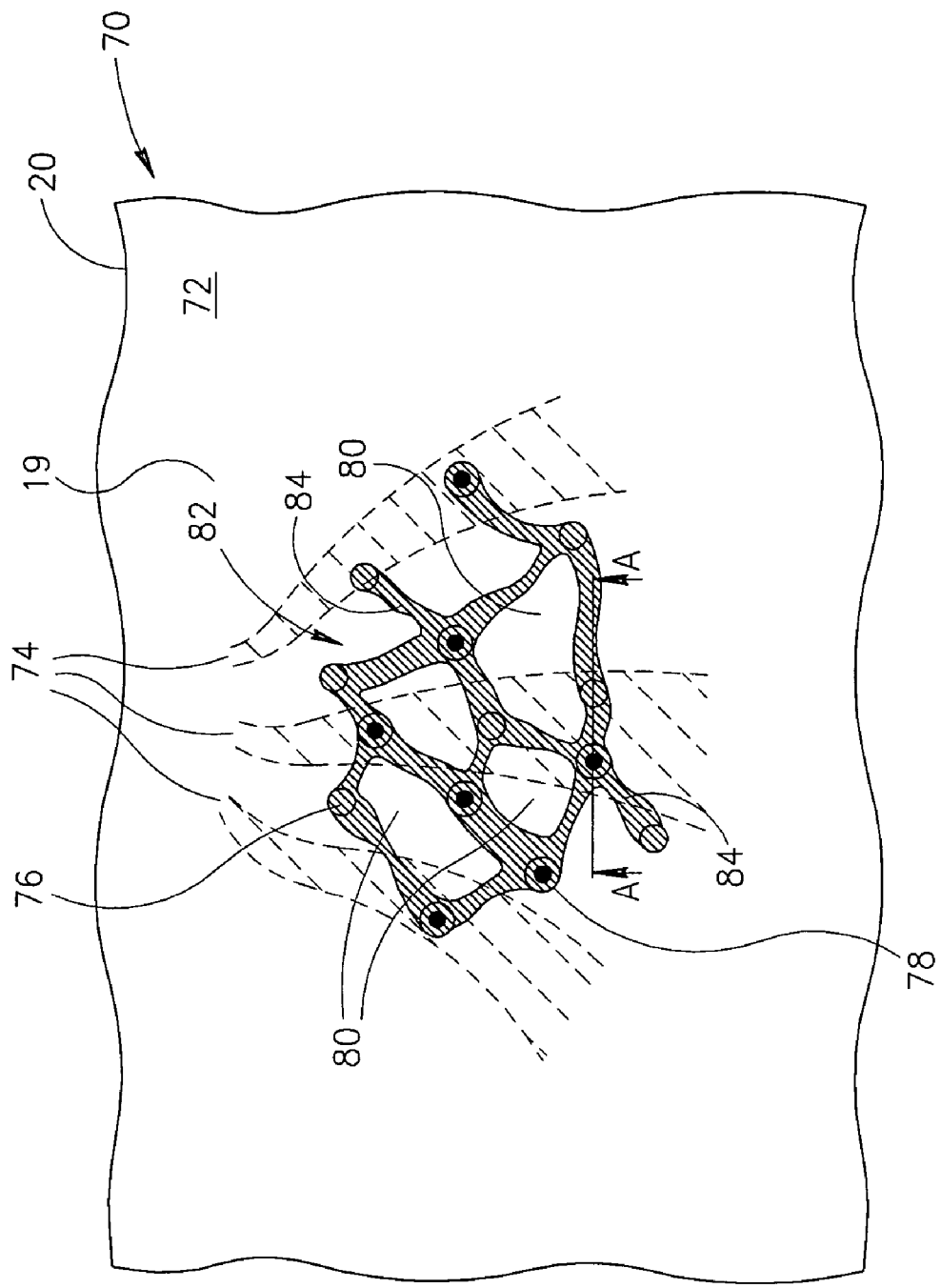

FIG. 3C schematically shows a plan view of cosmetic layer 19 after its volume has shrunk from loss of water. As a result of shrinkage, voids 80 form in cosmetic layer 19 and the layer is transformed from a relatively homogeneous layer covering a continuous region of skin 70 to a network 82 of strands 84 covering the skin region. Network 82 is anchored to skin 70 by hydrophilic and hydrophobic tendrils 77 and 85 (FIG. 3B) that protrude respectively into sweat gland ducts 76 and hair follicles 78 in skin 70. Each strand 84 contains aqueous slurry of filaments of hydrophilic particles 22 and adhered water molecules and hydrophobic particles 24. As a result of attractive forces between the particles and between the particles and water in the slurry, each strand tends to contract along its length with substantial force as it loses water. The contractive forces generated by strands 84 in network 82 apply forces to wrinkle furrows 74 in skin 70 that tend to pull out and flatten the wrinkle furrows.

Figure 3D:
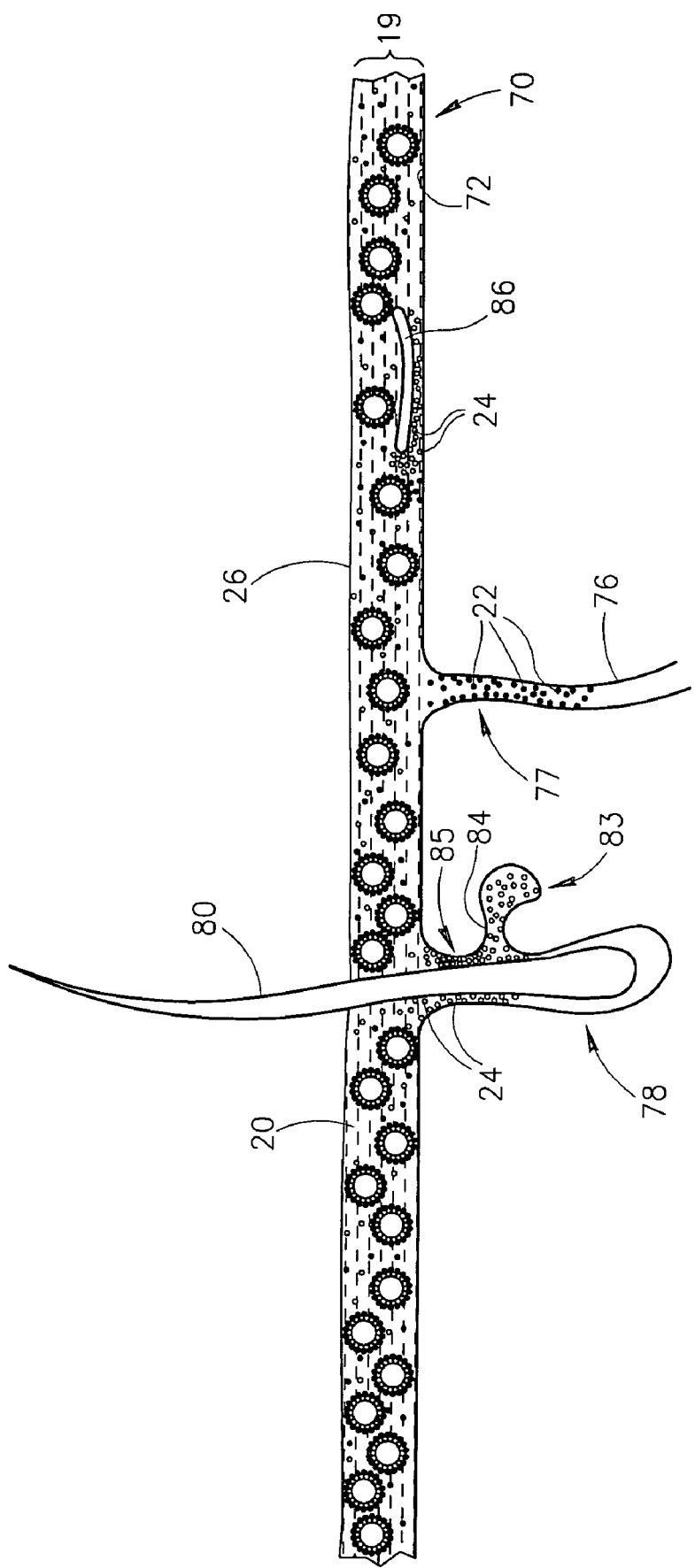

FIG. 3D schematically shows a cross section view of skin 70 and network 82 along line A-A shown in FIG. 3C which is the same line shown in FIG. 3A along which the cross-section view shown in FIG. 3B is taken. The cross-section view schematically shows the cosmetic affect of cosmetic emulsion 20 in ameliorating wrinkling in skin 70 during the application period of emulsion 20 to the skin. Wrinkle furrow 74 shown in FIG. 3B is substantially flattened in FIG. 3D. It is noted that in an experiment carried out by the inventor, depth of a relatively deep wrinkle furrow in a patient's skin was reduced by about 2 mm during an application period of a cosmetic emulsion similar to cosmetic emulsion 20.

Also, as shown in FIG. 3D, during the application period a sufficient quantity of hydrophobic particles 24 and water have become lodged under dead skin cell 86 so that the skin cell is detached from surface 72 of skin 70. When emulsion 20 is removed from skin 70 dead skin cell 86 is removed with the emulsion, leaving a fresher more vibrant looking region of skin where previously the dead skin cell was attached.

It is noted that network 82 of strands 84 adheres tenaciously to skin 70. In some embodiments of the present invention after network 82 is formed, excess emulsion is removed from skin 70 so as to leave network 82 substantially in place. This may be accomplished for example by gentle washing of the skin with water. Network 82 is substantially invisible, or may be easily camouflaged with suitable makeup, and the inventors have found that it can remain in place for periods of hours after treatment. In accordance with an embodiment of the present invention, anti-wrinkling action of network 82 in the region of skin on which it is located is "resurrected" by simply applying water to the skin. Network 82 absorbs some of the applied water causing strands 84 to tend to relax and elongate, relaxing thereby tension on the skin. Subsequently, network 82 releases water into the skin, as a result of which, strands 84 will again tend to contract and flatten wrinkles in the skin.

In some embodiments of the present invention, anti-wrinkling action is resurrected by applying a suitable cream, such as a moisturizing cream or a nutritional cream such as a cream comprising vitamin A or beta-carotene, having a component that is absorbed by the network and subsequently released to the skin. The component of the cream absorbed by the network and released to the skin may be an oil and/or water.

A region of skin treated with an emulsion, in accordance with an embodiment of the present invention, similar to emulsion 20 can therefore reduce wrinkling and keep the region of skin looking fresh and vibrant for an extended period of time by periodically applying water to the treated skin.

The functioning of a cosmetic powder, in accordance with an embodiment of the present invention, similar to cosmetic powder 50 is similar to the functioning of cosmetic emulsion 20 described above. When the powder is applied to the skin, shells in the powder that encapsulate water rupture and release the water they contain. The water and hydrophilic and hydrophobic particle "debris" from the shells form a cosmetic layer on the skin similar to cosmetic layer 19 shown in FIGS. 3A-3D.

The powder form of a cosmetic substance in accordance with an embodiment of the present invention however generally produces a thinner, less visible cosmetic layer on the skin than the emulsion form of the cosmetic substance. It is therefore generally more convenient for use as a cosmetic to maintain skin appearance when in public. For example a man or woman can conveniently carry the powder form of the cosmetic to freshen up his or her skin during a "powder break" to the bathroom during an evening out.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required or present in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. A powder comprising:
water;
hydrophilic oxide particles; and
hydrophobic oxide particles;
wherein the water is encapsulated in shells comprising an external layer of hydrophobic oxide particles and an internal layer of hydrophilic oxide particles adjacent to the layer of hydrophobic oxide particles.

2. A powder according to claim 1 wherein oxide hydrophilic particles are dispersed in the encapsulated water and form with the water a gel structure having filaments of oxide hydrophilic particles to which water molecules adhere.

3. A powder according to claim 1 wherein the hydrophobic oxide particles have a characteristic specific surface greater than about 100 m2/g.

4. A powder according to claim 2 wherein the hydrophobic oxide have a characteristic specific surface greater than about 100 m2/g.

5. A powder according to claim 1 wherein a relative concentration Cphil by weight of the oxide hydrophilic particles in the powder satisfies an equation Cphil=Kphil/Sphil where Sphil is a characteristic specific surface of the oxide hydrophilic particles and Kphil is a constant having a value between about 20 m2/g and about 50 m2/g.

6. A powder according to claim 5 wherein Kphil has a value between about 30 m2/g and about 40 m2/g.

7. A powder according to claim 1 wherein the hydrophilic oxide particles have a specific surface greater than about 100 m2/g.

8. A powder according to claim 5 wherein the hydrophilic oxide particles have a specific surface greater than about 100 m2/g.

9. A powder according to claim 6 wherein the hydrophilic oxide particles have a specific surface greater than about 100 m2/g.

10. A powder according to claim 1 wherein a characteristic diameter of hydrophilic oxide particles is between about 5 nm and about 150 nm.

11. A powder according to claim 2 wherein a characteristic diameter of hydrophilic oxide particles is between about 5 nm and about 150 nm.

12. A powder according to claim 1 wherein the shells have a characteristic average diameter in a range from about 1 micrometer to about 20 micrometers.

13. A powder according to claim 2 wherein the shells have a characteristic average diameter in a range from about 1 micrometer to about 20 micrometers.

14. A powder according to claim 1 wherein the hydrophilic oxide particles comprise oxide particles having surfaces covered with non-polar radicals.

15. A powder according to claim 14 wherein the hydrophilic oxide particles comprise a mix of hydrophilic oxide particles, said mix comprising a first type of hydrophilic oxide particles formed from particles based on a first oxide and at least one second type of hydrophilic oxide particles formed from particles based on a second oxide different from the first oxide.

16. A powder according to claim 14 wherein the oxide particles are selected from the group consisting of SiO2, Al2O3, TiO2, Fe2O3 and MnO particles.

17. A powder according to claim 14 wherein the polar radicals are selected from the group consisting of OH, CaCO3, CuSO4, and CaSO4.

18. A powder according to claim 1 wherein the hydrophobic oxide particles comprise oxide particles having surfaces covered with non-polar radicals.

19. A powder according to claim 18 wherein the hydrophobic oxide particles comprise a mix of hydrophobic oxide particles, said mix comprising a first type of hydrophobic oxide particles formed from particles based on a first oxide and at least one second type of hydrophobic oxide particles formed from particles based on a second oxide different from the first oxide.

20. A powder according to claim 18 wherein the oxide particles are selected from the group consisting of SiO2, Al2O3, TiO2, Fe2O3 or MnO particles.

21. A powder according to claim 1 wherein a substance beneficial for skin care is present in the water.

22. A powder according to claim 21 wherein the substance is an oil.

23. A powder according to claim 21 wherein the substance is vitamin A.

24. A powder according to claim 21 wherein the substance is beta carotine.

25. A method of reducing wrinkling in a region of skin comprising:
applying a powder in accordance with claim 1 to the region so that shells in the powder rupture and release their water content and the released water, hydrophilic particles and hydrophobic particles in the ruptured cells form a layer on the region; and
waiting a sufficient period of time so that at least portion of water in the layer is absorbed by the region and the volume of the layer shrinks so that the layer transforms into a network of strands on the region, which network is anchored to the skin by attraction of hydrophilic and hydrophobic particles to the skin and tends to contract as water is absorbed from the network.

26. A method according to claim 25 and comprising applying water to the region of skin after the network is formed so that the network absorbs water and expands and subsequently releases water to the skin and contracts again.

27. A method according to claim 25 and comprising applying a substance comprising a component that is absorbed by the network and the skin to the region of skin after the network is formed so that the network absorbs the component and expands and subsequently releases the component to the skin and contracts again.

28. A method according to claim 27 wherein the component is an oil.

29. A method according to claim 27 wherein the component is vitamin A.

30. A method according to claim 27 wherein the component is beta carotine.

31. A method of forming a powder comprising water, the method comprising:
forming a solution of water and hydrophilic oxide particles;
adding a quantity of hydrophobic oxide particles to the solution to form a mixture;
causing the gas to cavitate so that droplets of the water are encapsulated in shells of hydrophilic and hydrophobic particles and wherein the amounts of hydrophobic and hydrophilic oxide particles in the mixture are enough to form a sufficient number of shells so that substantially all the water in the mixture can be contained in encapsulated water droplets.

* * * * *